(12) United States Patent
Di Tullio et al.

(10) Patent No.: US 11,071,459 B2
(45) Date of Patent: Jul. 27, 2021

(54) SURFACE TISSUE TRACKING

(71) Applicant: KONINKLIJKE PHILIPS N.V., Eindhoven (NL)

(72) Inventors: Alessandra Di Tullio, Eindhoven (NL); Franciscus Hendrikus Van Heesch, Eindhoven (NL); Caifeng Shan, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 87 days.

(21) Appl. No.: 16/467,501

(22) PCT Filed: Dec. 8, 2017

(86) PCT No.: PCT/EP2017/082013
§ 371 (c)(1),
(2) Date: Jun. 7, 2019

(87) PCT Pub. No.: WO2018/104518
PCT Pub. Date: Jun. 14, 2018

(65) Prior Publication Data
US 2019/0365235 A1 Dec. 5, 2019

(30) Foreign Application Priority Data
Dec. 8, 2016 (EP) .................................... 16202834

(51) Int. Cl.
*A61B 5/00* (2006.01)
*G06T 7/246* (2017.01)

(52) U.S. Cl.
CPC ............ *A61B 5/0077* (2013.01); *A61B 5/442* (2013.01); *A61B 5/443* (2013.01); *A61B 5/444* (2013.01); *A61B 5/448* (2013.01); *A61B 5/489* (2013.01); *A61B 5/7221* (2013.01); *G06T 7/248* (2017.01); *G06T 2207/30088* (2013.01)

(58) Field of Classification Search
CPC ......... A61B 5/442; A61B 5/443; A61B 5/444; A61B 5/448; A61B 5/489; A61B 5/441; G06T 2207/30088
See application file for complete search history.

(56) References Cited

U.S. PATENT DOCUMENTS

| 6,126,636 A | 10/2000 | Naka |
| 2011/0026768 A1 | 2/2011 | Chari |

(Continued)

FOREIGN PATENT DOCUMENTS

WO 2007072356 A2 6/2007

OTHER PUBLICATIONS

International Search Report and Written Opinion of PCT/EP2017/082013, dated Mar. 26, 2018.

*Primary Examiner* — King Y Poon
*Assistant Examiner* — Michael Burleson

(57) ABSTRACT

Tissue surface tracking of tissue features is disclosed. First surface imaged features are tracked based on the first and second time spaced images at a first wavelength. Second surface imaged features are tracked based on the first and second time spaced tissue surface images at the second wavelength. Tracking metrics are obtained based on the tracking steps. The tracking steps are combined to provide a combined tracking metric. The combined tracking metric is used in a tissue surface navigation application.

20 Claims, 3 Drawing Sheets

(56) References Cited

U.S. PATENT DOCUMENTS

2011/0304720 A1* 12/2011 Kumar ............... G06K 9/00892
                                                             348/77
2012/0194662 A1   8/2012 Zhang
2012/0238882 A1   9/2012 Chou
2014/0350395 A1* 11/2014 Shachaf ................ G06T 7/0012
                                                             600/431
2016/0019421 A1*  1/2016 Feng .................. G06K 9/00617
                                                             382/117

* cited by examiner

SURFACE TISSUE TRACKING

CROSS-REFERENCE TO PRIOR APPLICATIONS

This application is the U.S. National Phase application under 35 U.S.C. § 371 of International Application No. PCT/EP2017/082013, filed on Dec. 8, 2017, which claims the benefit of European Patent Application No. 16202834.4, filed on Dec. 8, 2016. These applications are hereby incorporated by reference herein.

FIELD OF THE INVENTION

The technical field generally relates to surface tissue tracking. In particular, surface imaged features are utilized in a tracking process.

BACKGROUND OF THE INVENTION

WO2007072356 discloses a positioning system for a patient monitoring sensor or treatment device with imaging means for detecting a texture or pattern on the skin of a patient to identify a sensor location, an image processing unit which is adapted to learn the required location of a sensor by storing the local texture or pattern, and means for guiding a user to reposition the sensor or the user in the desired location by reference to the stored pattern. The texture or pattern may consist of a natural pattern such as a pattern of moles or varying skin color. However, optimal tracking of moles may require different tracking considerations than tracking varying color. Further, there are a range of other possible biomarkers that could be tracked that may not be optimally followed by the prior art system.

Thus, it is desired to provide more robust tracking systems and methods. It is further desirable to provide a tracking technique that allows for accurate and robust tracking of natural tissue surface features that can be used in many types of navigation applications.

SUMMARY OF THE INVENTION

Hence, there may be a need to provide an improved and facilitated way of tissue feature tracking.

Generally, embodiments of the present invention relate to tracking biomarkers using more than one tracking process. Each tracking process is tuned to different kinds of biomarkers by using differently spectrally filtered images in respective tracking processes. The tracking results from each tracking process are combined into a single tracking result for use in surface tissue based navigation applications.

The object of the present invention is solved by the subject-matter of the independent claims; wherein further embodiments are incorporated in the dependent claims.

In one aspect of the present disclosure, there is provided a tissue surface tracking system. The system comprises a data receiving module for receiving first and second time spaced tissue surface images, each time spaced tissue surface image includes image data at first and second different wavelengths. The system comprises first and second tracking modules. The first tracking module is configured to spatially track first tissue surface imaged features based on the first and second time spaced images at the first wavelength to responsively output at least one first tracking metric. The second tracking module is configured to spatially track second tissue surface imaged features based on the first and second time spaced images at the second wavelength and to responsively output at least one second tracking metric. A combination module is configured to combine the at least one first and the at least one second tracking metric and to responsively output at least one combined tracking metric for use in a tissue surface navigation application. The first and second wavelengths are tuned to different kinds of biomarkers. In other words, the first wavelength is more suited to detecting and tracking a first kind of biomarker than the second wavelength whereas the second wavelength is more suited to detecting and tracking a second kind of biomarker than the first wavelength, wherein the first and second kinds of biomarker are different.

By running tracking modules that operate on different wavelength images in parallel, it is possible to focus on different surface imaged features to provide for a more robust tracking system. For example, skin condition variation can make it difficult for one tracking module and single imaging band to successfully and accurately track tissue features. Different wavelength images can be more suited to different surface features. The present application addresses this problem by running tracking modules in parallel and combining output tracking metrics to provide for a more reliable system. In this way, the source of data operated upon by the tracking modules can be optimized for biomarker kind.

The tissue surface images may be skin images. The first and second tissue surface images may be obtained by a multispectral camera. The tissue surface imaged features may be biomarkers. The time spaced images may comprise reference and subsequent images. The tracking metrics may comprise spatial displacement information between time spaced images, such as comprising a displacement vector.

In an embodiment, the first tracking module is configured to operate a first tracking algorithm that is tuned to tracking a first kind of biomarker and the second tracking module is configured to operate a second tracking algorithm that is tuned to tracking a second kind of biomarker. Preferably, the first and second tracking algorithms are different.

For example, the tracking modules can operate different image filters, different segmentation approaches, different resolution levels, can be trained to focus on different types of features in order to be optimized for allowing identification of specific biomarkers. In a further embodiment, the tracking modules are tuned to specific biomarkers and the imaging wavelength is also optimized for accentuating that kind of biomarker.

In an embodiment, the system comprises at least one quality assessment module configured to assess quality of tracking performance for the first tracking module and to responsively output at least one first weighting metric and configured to assess quality of tracking performance for the second tracking module and to responsively output at least one second weighting metric. The combination module is configured to combine the at least one first and the at least one second tracking metric adaptively based on the at least one first weighting metric and the at least one second weighting metric. In an embodiment, the combination module is configured to combine the at least one first tracking metric and the at least one second tracking metric using a weighting algorithm in which relative weights of the at least one first tracking metric and the at least one second tracking metric are determined based on the at least one first weighting metric and the at least one second weighting metric. According to such features, the combination of tracking metrics is adapted depending upon tissue conditions. That is, the performance of certain tracking modules will be dependent upon location and upon the subject. By continually assessing tracking performance, different weights to differently performing tracking modules can be assigned such that the combination of tracking metrics takes into account relative performance of each module.

In an embodiment, the first tracking module is configured to determine the at least one first tracking metric using at least one of feature based tracking and intensity based tracking and the second tracking module is configured to determine the at least one second tracking metric using at least one of feature based tracking and intensity based tracking.

In an embodiment, the first tracking module and the second tracking module are respectively configured to track different kinds of biomarkers, wherein a first kind of biomarkers may be superficial skin structures and a second kind of biomarkers may be subsurface features. For example, the first kind of biomarkers are selected from the group of moles, hairs, freckles, pores, spots, melanin pigment, depressions, surface roughness, and the second kind of biomarkers may comprise veins or arteries.

The system may comprise a camera for capturing the first and second time spaced images at different spectral bands. The use of different spectral bands allows optimal detection of different tissue surface features.

The system of the present disclosure can be used in numerous applications that require or can make use of surface tissue navigation based on the combined tracking metric. For example, an image guided surgery or medical intervention system can incorporate the present system as can a system for registering intraoperative imaging data, preoperative imaging data or a combination of intraoperative and preoperative imaging data. The system can be comprised in a skin monitoring or skin diagnostics system. For example, the skin monitoring system may monitor changes in potentially diseased skin features such as moles identified as being suspicious. A further application would be consumer electronics products such as a hair removal device, a hair cutting device, a hair grooming device and a teeth cleaning device.

In another aspect of the present disclosure, there is provided a method for tissue surface tracking. The method comprises receiving first and second time spaced tissue surface images, each time spaced tissue surface image including image data at first and second different wavelengths. The method comprises tracking first surface imaged features based on the first and second time spaced images at the first wavelength and responsively outputting at least one first tracking metric. The method comprises tracking second surface imaged features based on the first and second time spaced tissue surface images at the second wavelength and responsively outputting at least one second tracking metric. The method comprises combining the at least one first and the at least one second tracking metric and responsively outputting at least one combined tracking metric. The method further comprises using the combined tracking metric in a tissue surface navigation application such as any one of the applications described above.

In embodiments, the method is computer implement through at least one processor executing computer readable instructions. The images may be acquired through an imaging device such as a camera. The method may comprise outputting the combined tracking metric to a system comprising a computer implemented tissue surface navigation application that uses the combined tracking metric as part of navigation control.

In an embodiment, the method comprises assessing quality of tracking performance for the first tracking module and responsively determining at least one first weighting metric and assessing quality of tracking performance for the second tracking module and responsively determining at least one second weighting metric. In a further embodiment, the step of combining the at least one first tracking metric and the at least one second tracking metric comprises using a weighting algorithm in which relative weights of the at least one first tracking metric and the at least one second tracking metric are determined based on the at least one first weighting metric and the at least one second weighting metric.

In an embodiment, the step of tracking first surface imaged features comprises operating a first tracking algorithm optimized with respect to a first kind of surface imaged features and the step of tracking second surface imaged features comprises operating a second tracking algorithm optimized with respect to tracking a second, different, kind of surface imaged features.

In yet another aspect of the present disclosure, there is provided a computer program element adapted to implement a systems and methods as described herein when executed by at least one processor.

In yet another aspect, there is provided a computer readable medium having stored thereon the program element.

These and other aspects of the invention will be apparent from and elucidated with reference to the embodiment(s) described hereinafter.

DESCRIPTION OF THE DRAWINGS

The exemplary embodiments will hereinafter be described in conjunction with the following drawing figures, wherein like numerals denote like elements, and wherein.

DETAILED DESCRIPTION OF THE EMBODIMENTS

The following detailed description is merely exemplary in nature and is not intended to limit the application and uses. Furthermore, there is no intention to be bound by any expressed or implied theory presented in the preceding technical field, background, brief summary or the following detailed description.

Figure 1:
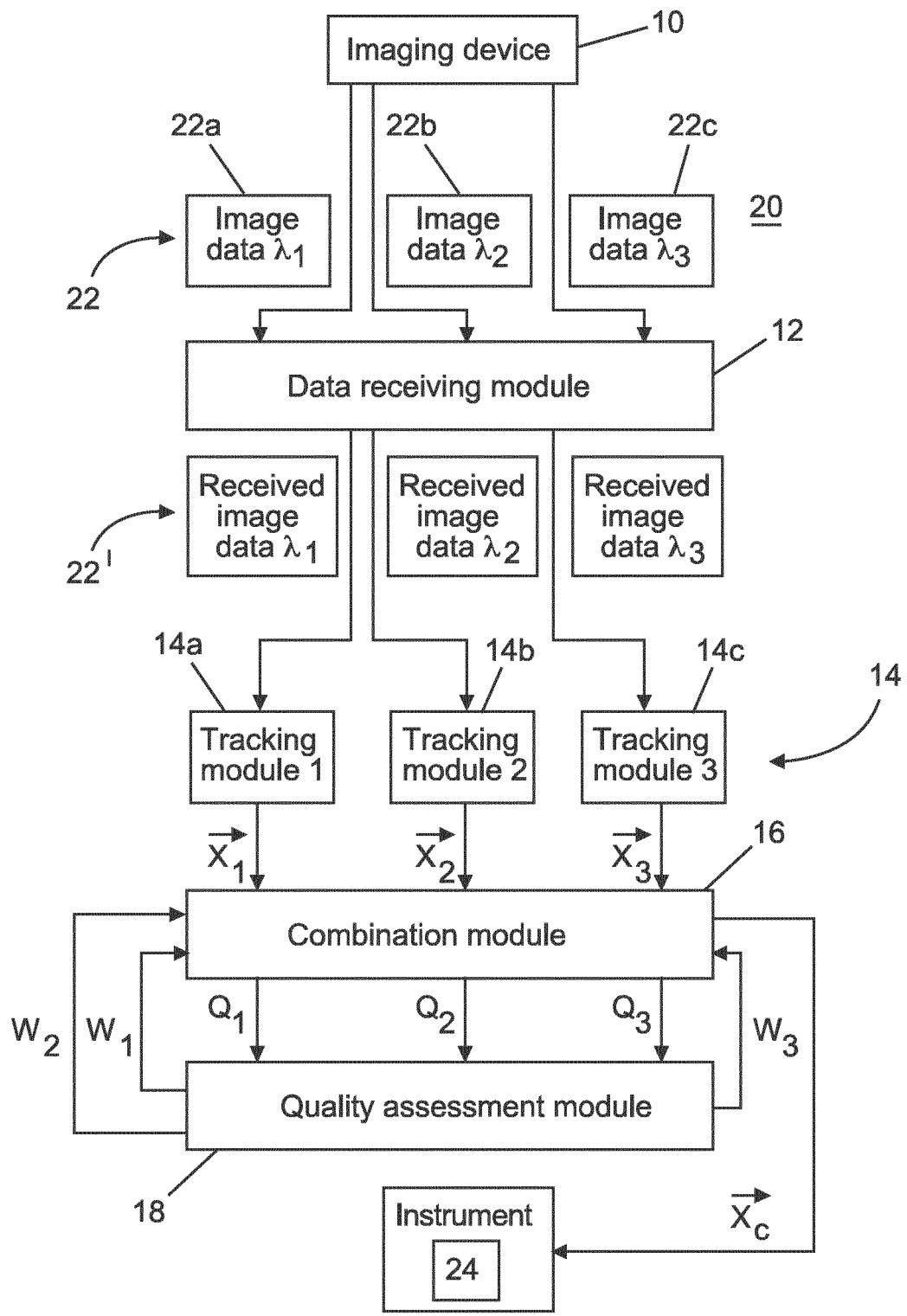
FIG. 1 is a schematic functional block diagram of a system for tracking tissue surfaced features according to an exemplary embodiment of the present disclosure, wherein the system diagram shows exemplary modules and data transformations by the system modules.

FIG. 1 is a functional block diagram of a system 20 for tissue surface tracking according to an exemplary system. FIG. 1 shows processing modules, the flow of data and transformations in the data performed by the various processing modules of the tracking system 20.

As used herein, the term module refers to an application specific integrated circuit (ASIC), an electronic circuit, a processor (shared, dedicated, or group) and memory that executes one or more software or firmware programs, a combinational logic circuit, and/or other suitable components that provide the described functionality. In particular, the modules described herein include at least one processor, a memory and computer program instructions stored on the memory that can be executed by the at least one processor for implementing the various functions and processes described herein with respect to the modules and also described with respect to the flowchart of FIG. 2. Although separate modules are described herein for particular functions, this does not exclude an integrated topology. Further, the shown modules may be divided into further sub-modules. The modules are in communication with one another, for example through a data bus, as necessary to implement the features, processes and systems described herein.

FIG. 1 shows an imaging device 10 for capturing plural time spaced images 22 at different spectral bands. The imaging device 10 may be an optical imaging device such as a camera. The imaging device 10 is configured to capture sequential images of an area of interest of a tissue surface (e.g. skin). The imaging device 10 is multispectral allowing plural images to obtained at different wavelengths (including different wavelength bands) and to obtain such multispectral images at successive time intervals, e.g. according to a set frame rate of the imaging device 10. The imaging device 10 may include plural filters, each designed to image different tissue surface visible features at a specific wavelength or wavelengths. The filters may be implemented by a physical filter or a combination of a physical filter and an image processing filter performed by at least one processor. The imaging device 10 may include separate arrays of imaging pixels, e.g. through separate cameras, in order to obtain image data 22 at different wavelengths.

The imaging device 10 may be configured to capture images 22 at respective wavelengths that are optimized for specific anatomical features. For example, an infrared wavelength can be used specifically for tracking veins and an ultraviolet wavelength can be used specifically for tracking moles and freckles. That is, certain wavelengths are able to accentuate specific surface tissue biomarkers. The imaging device can, in embodiments, capture images 22 at wavelengths that are optimal for respective biomarkers. Human tissue is partially transparent for visual and near-IR wavelengths, allowing surface features such as melanin pigment and hairs, and subsurface features like veins or arteries to be identified. Light with wavelengths closer to ultraviolet will be optimal for superficial skin features such as moles and freckles.

In one exemplary implementation of the system 20, at least three images 22a, 22b, 22c are obtained by the imaging device 10. The imaging device 10 may utilize different wavelength filters, such as filters for isolating the images 22a, 22b, 22c at wavelengths of 450 nm, 680 nm and 880 nm, to obtain each of the images 22a, 22b, 22c. These exemplary wavelengths are tuned, for instance, to moles or other melanine pigment features, surface irregularities such as wrinkles, and subsurface veins, respectively.

In the exemplary system of FIG. 1, a data receiving module 12 is shown for receiving first and second time spaced tissue surface images 22, each time spaced tissue surface image including image data at first and second different wavelengths. The data receiving module 12 is configured to receive image data 22a, 22b, 22c at different wavelengths $\lambda_1$, $\lambda_2$, $\lambda_3$. Image data 22 can be received at spaced time intervals during which displacement may have occurred in the image content. The present disclosure utilizes tracking modules 14 to keep track of the movement as described further in the following.

The data receiving module 12 may comprise an input data interface for receiving the image data 22. The input data interface may be a networked component allowing the image data 22 to be received over a wireless network, such as over the internet or intranet. In the exemplary system of FIG. 1, the image data 22 is received from the imaging device 10. The data receiving module 12 may further comprise a data output interface for providing the time spaced image data 22 to respective tracking modules 14a, 14b, 14c, where each tracking module 14a, 14b, 14c receives imaging data filtered at different wavelengths (including different wavelength bands) $\lambda_1$, $\lambda_2$, $\lambda_3$. The data receiving module 12 may include a processor and executable computer program instructions for directing receipt of the image data 22 and output of the received image data 22' to respective tracking modules 14a, 14b, 14c.

In the exemplary system 20 of FIG. 1, there is provided first, second and third tracking modules 14a, 14b, 14c. Each tracking module 14 is configured to spatially track tissue surface imaged features, e.g. biomarkers, based on time spaced image data 22' received from the data receiving module 12. The tracking modules 14a, 14b, 14c are respectively configured to output a tracking metric $\vec{X}_1$, $\vec{X}_2$, $\vec{X}_3$. The tracking metric $\vec{X}_1$, $\vec{X}_2$, $\vec{X}_3$ may represent spatial displacement in time spaced images 22'. For example, the tracking metric $\vec{X}_1$, $\vec{X}_2$, $\vec{X}_3$ may comprise a spatial displacement vector defining displacement in time spaced images in three dimensions, which may include a rotational component and/or a linear displacement in two or three-dimensional Cartesian space. The tracking modules 14 may include an input data interface for receiving image data 22' from the data receiving module 12 and an output data interface for outputting at least one tracking metric $\vec{X}_1$, $\vec{X}_2$, $\vec{X}_3$ and optionally a tracking quality or performance metric $Q_1$, $Q_2$, $Q_3$, as will be discussed further below. The tracking modules 14 may further comprise at least one processor and computer readable instructions executable by the at least one processor to implement the tissue surface tracking algorithms described herein. Further, the processor and computer readable instructions operate to determine at least one quality metric $Q_n$ for each tracking module 14a, 14b, 14c.

Each tracking module 14a, 14b, 14c is configured to operate a different tracking algorithm. An exemplary tracking algorithm will be described below with reference to FIG. 3. Each tracking algorithm is tuned to track different kinds of biomarker. Exemplary biomarkers that can be imaged by tissue surface imaging, include moles, hairs, freckles, spots, melanin pigment, depressions, surface roughness and veins. For example, a tracking algorithm that operates on surface roughness would find the best correlation between displaced image intensities of each image pair. Typically image patches of each image are normalized and the intensity differences between these normalized patches are used as a matching error. A patch pair with the lowest error is considered the best displacement candidate. An exemplary tracking algorithm that operates on veins, instead would transform the images first to feature vectors (for example by applying the scale-invariant feature transform SIFT algorithm) and calculate descriptors for each of these vectors. The displacement between matching descriptors is then used to calculate the displacement between image pairs. Accordingly, one tracking module 14a, 14b, 14c may use intensity based tracking tuned to a specific biomarker and another tracking module 14a, 14b, 14c may use feature based tracking tuned to a different biomarker. Further, the tracking modules 14a, 14b, 14c may utilize different reference images (reference descriptors) in feature based tracking that correspond to the specific biomarker being sought. As has been explained in the foregoing, the image data 22' may also be spectrally selected so as to maximize an ability to identify in the image data 22' specific biomarkers. As such, not only are the tracking algorithms of the tracking modules 14 biomarker tuned, but the image data 22' itself received by each tracking module 14 is filtered to optimize identification of its biomarker. By running multiple spatial trackers 14 in parallel for image data 22' at different wavelengths, a surface tissue location metric $\vec{X}_1$, $\vec{X}_2$, $\vec{X}_3$ can be obtained that is robust to local anatomical differences in surface tissue (e.g. presence and amount of hair, spots, and veins).

Figure 3:
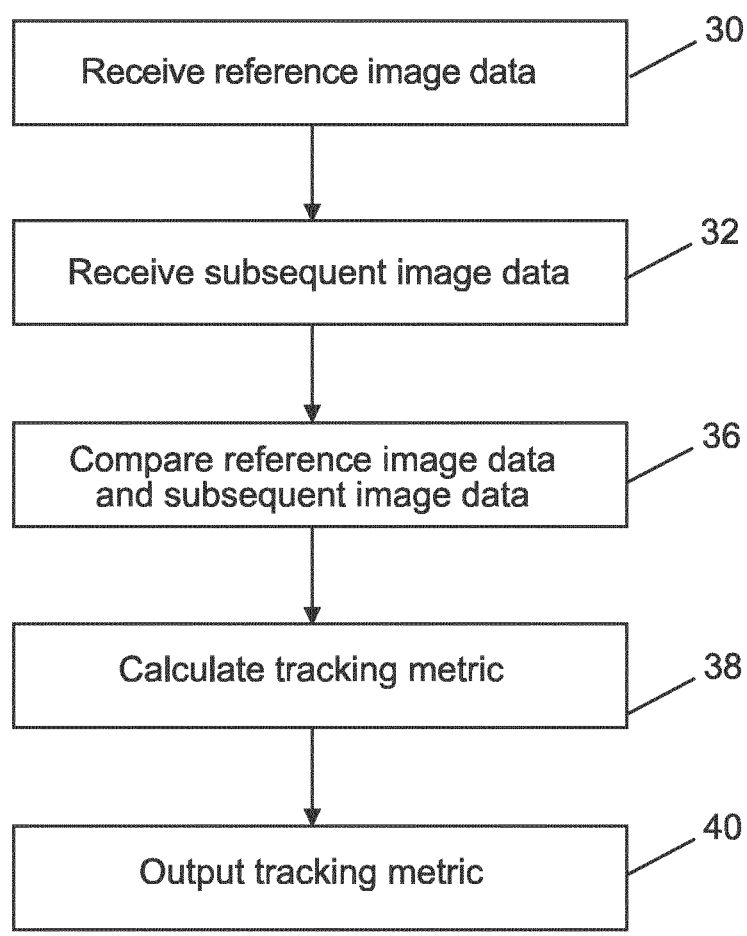
FIG. 3 is a flowchart illustrating steps of a tracking algorithm according to an exemplary embodiment.

Referring to FIG. 3, an exemplary tracking algorithm 50 for each module 14a, 14b, 14c will be discussed at a general level of detail. Tissue surface tracking algorithms per se are known to the skilled person and the present description is representative of one exemplary implementation. The tracking algorithm 50 includes receiving steps 30, 32 for receiving time spaced reference image data and subsequent image data. The reference and subsequent image data are taken from the time spaced image data 22' described in the foregoing. In step 36, the reference and subsequent image data is compared to register or match patterns of biomarkers in the reference image data and the subsequent image data. The comparison step 36 may make use of feature based tracking or intensity based tracking. In feature based tracking, patterns of surface tissue features in the subsequent and reference image data are identified and matched or registered in the comparison step 36. In intensity based tracking, image patches are defined in the reference and subsequent image data, which are compared in the comparison step 36, thereby allowing intensity based patterns of biomarkers in the reference and subsequent image date to be matched or registered. In both intensity based and feature based methods, a subsequent step 40 can be implemented by which a relative position or displacement metric, as one example of the aforementioned tracking metric, is determined based on the comparison step 36. In particular, displacement in feature or intensity patterns between the reference and subsequent image data allows a tracking metric to be determined in step 38 such as the displacement vectors $\vec{X}_1$, $\vec{X}_2$, $\vec{X}_3$ described above. The compared image data may be chromatic or monochrome. In step 40, the tracking algorithm, implemented by a tracking module 14, is output for subsequent processing as described in the following.

Referring back to FIG. 1, each tracker module 14a, 14b, 14c derives a displacement metric $\vec{X}_n$ between previous (reference) and subsequent image data 22' based on a correspondence analysis of the image data 22' such as that described above with respect to step 36 of FIG. 3.

Continuing to refer to FIG. 1, the exemplary system 20 comprises a combination module 16 configured to combine the tracking metrics $\vec{X}_1$, $\vec{X}_2$, $\vec{X}_3$ to output a combined tracking metric $\vec{X}_C$. The combined tracking metric $\vec{X}_C$ is used in a tissue surface navigation application. Exemplary applications for the combined tracking metric $\vec{X}_C$ will be described hereinafter. The combined tracking metric $\vec{X}_C$ may be determined by an averaging function taking as inputs the tracking metrics $\vec{X}_1$, $\vec{X}_2$, $\vec{X}_3$. Example averaging functions include mean, median and mode functions. Accordingly, the combined tracking metric $\vec{X}_C$ may be an average displacement metric or an average displacement vector. The combination module 16 may comprise an input data interface for receiving the tracking metrics $\vec{X}_n$ from the tracking modules 14 and optionally for receiving weighting metrics $W_n$ from a quality assessment module 18 to be described in greater detail hereinafter. The combination module 16 may include a processor and computer readable instructions executable by the processor to implement the function of combining a plurality of input tracking metrics $\vec{X}_n$ as described. Further, the combination module 16 may include an output data interface for providing the combined tracking metric $\vec{X}_C$ to an instrument 24 that is configured to incorporate the combined tracking metric $\vec{X}_C$ as part of a control function based on skin surface navigation. Examples of the instrument 24 and control functions thereof will be described hereinafter.

In accordance with embodiments, the combination module 16 makes use of an averaging algorithm that is adaptive based on a quality assessment of each tracking module 14a, 14b, 14c. That is, a relative weight of contribution in the combined tracking metric $\vec{X}_C$ is adapted depending upon a determined quality of performance of each tracking module 14a, 14b, 14c. In particular, quality metrics $Q_1$, $Q_2$, $Q_3$ from each tracking module 14a, 14b, 14c can be compiled by the below described quality assessment module 18 to determine upon weighting metrics $W_1$, $W_2$, $W_3$ to be applied in the averaging algorithm for averaging the tracking metrics $\vec{X}_1$, $\vec{X}_2$, $\vec{X}_3$. In this way, an adaptive surface tissue tracking capability is provided that adapts determination of the combined tracking metric in accordance with the fact that different tracking modules (e.g. different tracking algorithms and/or different imaging wavelengths) will perform at different levels of quality depending on subject, body part, etc. As such, a location-independent, robust tracking solution is made possible.

In the exemplary system 20 of FIG. 1, a quality assessment module 18 is included. The quality assessment module 18 is configured to assess quality of tracking performance of tracking modules 14 based on the quality metrics $Q_1$, $Q_2$, $Q_3$ received from respective tracking modules 14a, 14b, 14c. The quality assessment module 18 is configured to process the quality metrics and determine upon a weighting factor $W_1$, $W_2$, $W_3$ for each tracking module 14a, 14b, 14c. The weighting factor may be determined based on a combination of more than one quality metric $Q_1$, $Q_2$, $Q_3$ received from respective tracking modules 14a, 14b, 14c indicative of quality of performance of the tracking module. The quality metrics $Q_n$ may be determined by respective tracking modules 14a, 14b, 14c based on a parameter representative of number or amount of biomarkers in the time spaced image data 22', a parameter representative of number or amount of match or registration between time spaced image data 22', and/or a parameter representative of quality of match, e.g. representative of closeness of match or minimal error in comparing the time spaced image data 22'.

With reference to the discussion of tracking algorithms provided above with respect to FIG. 3, for feature based tracking, like that used for vein tracking, the quality metric $Q_n$ can be determined by the number of features (e.g. veins) that are identified in the time spaced image data 22' and/or the number features matched in the time spaced image data 22', the match error between features identified in the time spaced image data 22' (e.g. the successive appearance match) and/or a parameter representative of agreement between matched features in time spaced image data 22' (e.g. the displacement agreement between identified features). For intensity-based tracking, the quality metric $Q_n$ can be a function of the frequency content of defined image patches (e.g. the amount of detail) in the time spaced image data 22', the fit quality between patches (e.g. intensity difference) in the time spaced image data 22' and/or the agreement or inverse error of multiple correspondences between patches in the time spaced image data 22'.

The quality assessment module 18 may include an input data interface for receiving quality metrics $Q_n$ from the tracking modules 14. The quality assessment module may include a processor and computer readable instructions executable by the processor for assessing the various quality metrics $Q_n$ and determining, based on the quality metrics $Q_n$, weighting factors $W_n$ associated with each tracking module 14. The quality assessment module 18 may include an output data interface for providing the weighting factors Wn to the combination module 16.

In the exemplary system 20 of FIG. 1, the combination module 16 is configured to apply the weighting factors $W_n$ in the averaging algorithm to set a relative contribution of each tracking metric $\vec{X}_1$, $\vec{X}_2$, $\vec{X}_3$ to the combined tracking metric $\vec{X}_C$. For example, a weighted mean or weighted median may be executed by the combination module 16 based upon the weighting factors $W_n$ so as to provide a combined tracking metric that is adaptive to the quality of biomarkers in image data 22' with respect to both optimal wavelength and optimal tuning of tracking algorithm.

In the exemplary system 20 of FIG. 1, the combined tracking metric $\vec{X}_C$ is output to an instrument 24. The instrument 24 may 8 be an image guided surgery or medical intervention system, a system for registering intraoperative/or imaging data, a skin monitoring or skin diagnostics system or a consumer electronics product such as a hair removal device, a hair cutting device, a hair grooming device and a teeth cleaning device.

In embodiments, the instrument 24 includes a control module 26. The control module 26 may alternatively be externally provided. The control module 26 is configured to determine upon at least one control function of the instrument 24 based on the combined tracking metric $\vec{X}_C$. That is, operation of the instrument 24 may be at least partly dependent on surface tissue navigation. Surface tissue navigation can be implemented using the combined tracking metric $\vec{X}_C$ according to schemes known to the skilled person.

In one example, the instrument 24 is an instrument for registering pre-operative and intra-operative imaging data such as CT or MRI imaging data. Alternatively or additionally, the instrument 24 is for registering successive intraoperative images or successive preoperative images such as MRI or CT images. Such an instrument 24 may comprise an imaging machine for invasive imaging of a patient. The pre-operative and the intra-operative image data are obtained simultaneously with imaging data 22 from the imaging device 10. The imaging device 10 has a known relationship with the invasive imaging machine. As such, biomarkers can be tracked from the imaging data 22 according to the methods and systems described herein to allow for registration of pre-operative and intraoperative imaging data. Such registration can be implemented in the control module 26 based at least partly on the combined tracking metric $\vec{X}_C$ and a display of registered preoperative and intraoperative images may be rendered.

In another example, the instrument 24 comprises an instrument for guiding a medical device. Accurate guidance may be established with reference to surface tissue biomarkers tracked according to the systems and methods described herein. The control module 26 may be included in the medical device guidance instrument and can establish a navigation control function at least partly based on the combined registration metric $\vec{X}_C$.

In yet another example, a hair or skin treatment device (e.g. hair cutting device) may surface tissue navigate based on tracking biomarkers according to the systems and methods described herein. The control module 26 may be included into the hair or skin treatment device to establish at least one hair or skin treatment control function based at least partly on the combined tracking metric $\vec{X}_C$.

In a further example, the instrument 24 is an instrument for monitoring over time potentially diseased skin features. For example, suspicious moles may be monitored over time, where such moles may be cancerous. The skin features can be identified and monitored with reference to biomarkers tracked according to systems and methods described herein. For example, shape, location, size and/or color change can be monitored. The control module 26 may be included into such an instrument for monitoring to establish at least one monitoring function (such as skin feature identification, skin feature measuring, skin feature change determination) at least partly based on the combined tracking metric $\vec{X}_C$.

Other systems and instruments that are controlled based at least partly on surface tissue navigation in order to perform a patient procedure can make use of surface tissue tracking systems and methods as described herein.

Figure 2:
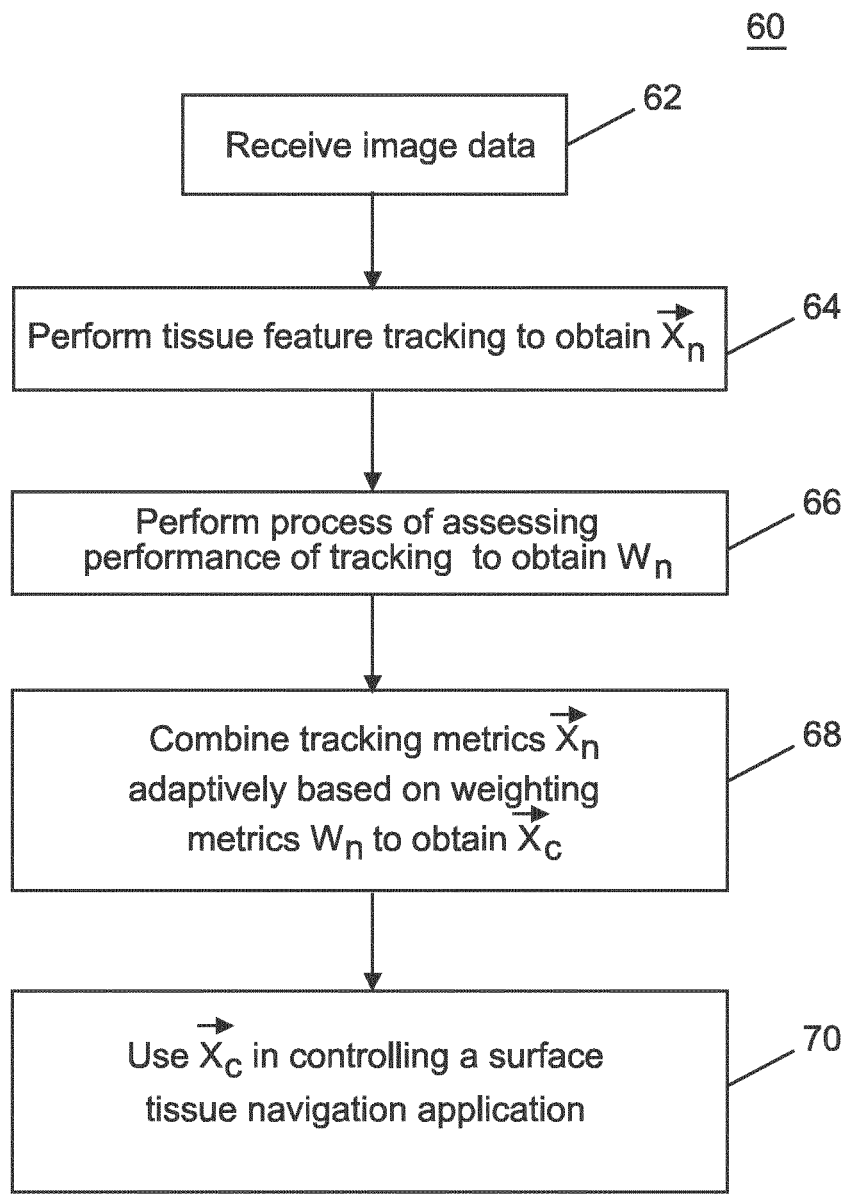
FIG. 2 is a flowchart illustrating steps of a method for tracking surface tissue features according to an exemplary embodiment.

A method 60 for tissue surface tracking according to the present disclosure is represented by the flowchart of FIG. 2. The method is, in embodiments, computer implemented by way of computer readable instruction being executed by a processor. The method is implemented, in embodiments, by the system 20 described with respect to FIG. 1.

In step 62, image data 22 is received through the data receiving module 12. The image data 22 includes time spaced multispectral data. The image data 22 may be obtained by a multispectral camera 10 operating different filters so that image data 22 is acquired at different wavelengths or spectral bands. Time spaced image data 22' at different wavelengths is respectively provided to different tracking processes.

In step 64, tracking processes are performed through the tracking modules 14 for tracking surface imaged features, e.g. surface tissue biomarkers. Respective tracking processes are performed on time spaced image data 22' filtered to specific wavelengths. In particular, spatial tracking of biomarkers from a reference image to a subsequent image is performed based on a correlation analysis of the reference and subsequent images. The tracking processes are respectively tuned to a specific biomarker kind and the received image data is also tuned to that biomarker kind. The tracking processes of step 64 produce tracking metrics $X_n$ for each of the tracking modules 14.

In step 66, a quality assessment process is performed through a combination of the tracking modules 14 and the quality assessment module 18 to produce weighting metrics $W_n$ for use by the combination module 16. The quality assessment process comprises, in embodiments, a sub-process of determining at least one quality metric $Q_n$ through each of the tracking modules 14. The at least one quality metric $Q_n$ is representative of a quality of tracking performance by the tracking modules 14. The weighting metrics or factors $W_n$ can be determined on the basis of the quality metrics $Q_n$.

In step 68, a quality adaptive combination of the tracking metrics $X_n$ obtained in step 64 is performed based on the weighting metrics $W_n$ obtained in step 66 to determined a combined tracking metric $\vec{X}_C$. The quality adaptive combination may comprise a weighted averaging algorithm such as weighted mean or weighted median. Different tracking algorithms and different wavelengths of imaging data will perform differently depending upon surface tissue conditions. The systems and methods described herein are able to prioritize better performing tracking processes in determining the combined tracking metric $\vec{X}_C$. Further, the processes of the method 60 of FIG. 3 are iteratively performed to allow for continual optimization as surface tissue conditions vary.

In step 70, the combined tracking metric $\vec{X}_C$ is used or outputted for use in a patient treatment, therapy or diagnosis application, e.g. as a control input of a patient treatment, therapy or diagnosis system, that operate surface tissue navigation. A number of examples of such applications are described above, such as CT or MRI imaging data registration, diseased skin feature monitoring, medical device navigation, hair or skin treatment application, etc.

It can be appreciated that surface tissue can vary considerably depending on location on a subject and from subject to subject. For example, different subjects and different surface locations will have varying amount of hair, spots, and veins. In the case of skin, the appearance of surface tissue can vary from very smooth (i.e. without color variations, hair or wrinkles) to very detailed (i.e. with melanin spots, hairs and surface roughness and pores). These variations are not only body location dependent (e.g. moles/freckles are more visible on the back, blood vessels on arm), but also dependent on subject, race, age and gender. The present disclosures offers a more robust solution to such variability in tissue conditions as it runs parallel tracking modules operating on images directed to different wavelengths, thereby allowing accentuation of different tissue features for tracking. Further, the tracking modules themselves may be differently algorithmically tuned to optimize tracking of different tissue features. Yet further, the combination of tracking results is adapted depending upon tracking performance so that output results are smooth irrespective of tissue conditions.

In another exemplary embodiment of the present invention, a computer program or a computer program element is provided that is characterized by being adapted to execute the method steps of the method according to one of the preceding embodiments, on an appropriate processing system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A tissue surface tracking system, the system comprising:
   a data receiver configured to receive first and second time spaced tissue surface images, each time spaced tissue surface image including image data at first and second different wavelengths, wherein the first and second wavelengths are tuned to different kinds of biomarkers;
   first and second tracking processors,
   wherein the first tracking processor is configured to spatially track first tissue surface imaged features based on the first and second time spaced images at the first wavelength to responsively output at least one first tracking metric, and
   wherein the second tracking processor is configured to spatially track second tissue surface imaged features based on the first and second time spaced images at the second wavelength and to responsively output at least one second tracking metric;
   at least one quality assessment processor configured to assess quality of tracking performance for the first tracking processor and to responsively output at least one first weighting metric and configured to assess quality of tracking performance for the second tracking processor and to responsively output at least one second weighting metric; and
   a combination processor configured to adaptively combine the at least one first and the at least one second tracking metric based on the at least one first weighting metric and the at least one second weighting metric and to responsively output at least one combined tracking metric for use in a tissue surface navigation application.

2. The system of claim 1,
   wherein the first tracking processor is configured to operate a first tracking algorithm that is tuned to tracking a first kind of biomarker and the second tracking processor is configured to operate a second tracking algorithm that is tuned to tracking a second kind of biomarker.

3. The system of claim 1, wherein the combination processor is configured to combine the at least one first tracking metric and the at least one second tracking metric using a weighting algorithm in which relative weights of the at least one first tracking metric and the at least one second tracking metric are determined based on the at least one first weighting metric and the at least one second weighting metric.

4. The system of claim 1, wherein the first tracking processor is configured to determine the at least one first tracking metric using at least one of feature based tracking and intensity based tracking and the second tracking processor is configured to determine the at least one second tracking metric using at least one of feature based tracking and intensity based tracking.

5. The system of claim 4, wherein the first wavelength is tuned towards superficial skin features as a first kind of biomarker, and the second wavelength is tuned towards subsurface features as a second kind of biomarker.

6. The system of claim 5, wherein the first kind of biomarker comprises at least one of the group of moles, hairs, freckles, pores, spots, melanin pigment, depressions, surface roughness.

7. The system of claim 5, wherein the second kind of biomarker comprises veins or arteries.

8. The system of claim 1, comprising a camera for capturing the first and second time spaced images at different spectral bands.

9. An image guided surgery or medical intervention system or a system for registering intraoperative imaging data, preoperative imaging data or a combination of intraoperative and preoperative imaging data comprising the system of claim 1.

10. A skin monitoring or skin diagnostics system comprising the system of claim 9.

11. A consumer electronics product comprising the system of claim 9, wherein the consumer electronics product is selected from the group of a hair removal device, a hair cutting device, a hair grooming device and a teeth cleaning device.

12. A method for tissue surface tracking, the method comprising:
    receiving first and second time spaced tissue surface images, each time spaced tissue surface image including image data at first and second different wavelengths tuned to different kinds of biomarkers;
    tracking a first kind of biomarkers as first surface imaged features based on the first and second time spaced images at the first wavelength and responsively providing at least one first tracking metric;
    tracking a second kind of biomarkers as second surface imaged features based on the first and second time spaced tissue surface images at the second wavelength and responsively providing at least one second tracking metric;
    determining at least a first quality metric and a second quality metric representative of a quality of a tracking performance;
    determining at least a first weighting metric and a second weighting metric on the basis of the quality metrics;
    adaptively combining the at least one first and the at least one second tracking metric based on the first and second weighting metrics, and responsively providing at least one combined tracking metric; and
    using the combined tracking metric in a tissue surface navigation application.

13. The method of claim 12, comprising combining the at least one first tracking metric and the at least one second tracking metric using a weighting algorithm in which relative weights of the at least one first tracking metric and the at least one second tracking metric are determined based on the at least one first weighting metric and the at least one second weighting metric.

14. The method of claim 12, further comprising determining the at least one first tracking metric using at least one of feature based tracking and intensity based tracking and determining the at least one second tracking metric using at least one of feature based tracking and intensity based tracking.

15. The method of claim 12, wherein the first wavelength is tuned towards superficial skin features as the first kind of biomarkers, and the second wavelength is tuned towards subsurface features as the second kind of biomarkers.

16. The method of claim 15, wherein the first kind of biomarkers comprises at least one of the group of moles, hairs, freckles, pores, spots, melanin pigment, depressions, surface roughness.

17. The method of claim 12, comprising combining the at least one first tracking metric and the at least one second tracking metric using a weighting algorithm in which relative weights of the at least one first tracking metric and the at least one second tracking metric are determined based on the at least one first weighting metric and the at least one second weighting metric.

18. A non-transitory computer readable medium having stored thereon instructions that when executed by at least one processor cause the at least one processor to:
receive first and second time spaced tissue surface images, each time spaced tissue surface image including image data at first and second different wavelengths tuned to different kinds of biomarkers;
track a first kind of biomarkers as first surface imaged features based on the first and second time spaced images at the first wavelength and responsively providing at least one first tracking metric;
track a second kind of biomarkers as second surface imaged features based on the first and second time spaced tissue surface images at the second wavelength and responsively providing at least one second tracking metric;
determine at least a first quality metric and a second quality metric representative of a quality of a tracking performance;
determine at least a first weighting metric and a second weighting metric on the basis of the quality metrics;
adaptively combine the at least one first and the at least one second tracking metric based on the first and second weighting metrics, and responsively providing at least one combined tracking metric; and
use the combined tracking metric in a tissue surface navigation application.

19. The non-transitory computer readable medium of claim 18, further comprising instructions, that when executed by the at least on processor, cause the at least one processor to determine the at least one first tracking metric using at least one of feature based tracking and intensity based tracking and determine the at least one second tracking metric using at least one of feature based tracking and intensity based tracking.

20. The non-transitory computer readable medium of claim 18, wherein the first wavelength is tuned towards superficial skin features as the first kind of biomarkers, and the second wavelength is tuned towards subsurface features as the second kind of biomarkers.

* * * * *